(12) United States Patent
Bevins, III et al.

(10) Patent No.: US 6,491,777 B1
(45) Date of Patent: Dec. 10, 2002

(54) METHOD OF MAKING NON-WOVEN COMPOSITE TRANSFER LAYER

(75) Inventors: Errette Shemmell Bevins, III, Waynesboro, VA (US); Jacqueline Willey, Mauldin, SC (US)

(73) Assignee: Polymer Goup, Inc., North Charleston, SC (US)

( * ) Notice: Subject to any disclaimer, the term of this patent is extended or adjusted under 35 U.S.C. 154(b) by 0 days.

(21) Appl. No.: 09/455,634

(22) Filed: Dec. 7, 1999

(51) Int. Cl.⁷ .......................... B32B 31/16; B32B 31/26
(52) U.S. Cl. .................. 156/167; 156/181; 156/183
(58) Field of Search .................. 156/167, 181, 156/183; 442/382, 392, 401; 604/378

(56) References Cited

U.S. PATENT DOCUMENTS

| | | | | |
|---|---|---|---|---|
| 4,717,329 A | * | 1/1988 | Packard et al. | 264/282 |
| 4,749,423 A | * | 6/1988 | Vaalburg et al. | 156/181 |
| 4,921,643 A | * | 5/1990 | Walton et al. | 264/282 |
| 5,041,255 A | * | 8/1991 | Zafiroglu | 264/288.8 |
| 5,078,935 A | * | 1/1992 | Kobayashi et al. | 264/103 |
| 5,491,016 A | * | 2/1996 | Kaiser et al. | 156/290 |
| 5,575,874 A | * | 11/1996 | Griesbach | 156/167 |
| 5,609,702 A | * | 3/1997 | Andersen | 156/183 |
| 5,704,101 A | * | 1/1998 | Majors et al. | 156/515 |
| 5,814,390 A | * | 9/1998 | Stokes et al. | 428/181 |
| 5,840,633 A | * | 11/1998 | Kurihara et al. | 156/229 |
| 6,054,202 A | * | 4/2000 | Takeuchi et al. | 442/382 |
| 6,254,821 B1 | * | 7/2001 | Fleissner | 156/167 |

FOREIGN PATENT DOCUMENTS

JP   8-176947   * 7/1996

* cited by examiner

Primary Examiner—Steven D. Maki
(74) Attorney, Agent, or Firm—Wood, Phillips, Katz, Clark & Mortimer

(57) ABSTRACT

A method for making a fluid transfer layer has steps of depositing a first non-woven layer on a support, depositing a second non-woven layer on the first layer, with the two layers having a different melting point. The two layers are then thermally bonded to one another in a heated calender nip, during which differential shrinkage occurs because of the two layers' different melting points. A micro-bulked profile results. The composite, micro-bulked web is then mechanically bulked to provide a macro-bulked profile. The resulting non-woven fabric has a high bulk, high resistance to pore structure collapse, high resistance to compression deformation, and is more economical to produce than prior art carded or bicomponent webs. An absorbent article has a porous topsheet, the fluid transfer layer of the invention underlying the topsheet, and an absorbent core.

18 Claims, 2 Drawing Sheets

METHOD OF MAKING NON-WOVEN COMPOSITE TRANSFER LAYER

FIELD OF THE INVENTION

The present invention relates generally to methods for making non-woven fabrics, and the fabrics produced thereby. More particularly, the present invention relates to methods of making composite non-woven webs useful as fluid transfer layers in absorbent articles, as well as the nonwoven webs produced thereby.

BACKGROUND OF THE INVENTION

Non-woven fabrics, because of their structure and low cost of production, have proven particularly useful as absorbent articles. By way of example, many diapers, adult incontinence products, and sanitary napkins are comprised of non-woven fabrics.

Within non-woven absorbent articles, it is known to provide an outer top sheet, an intermediate fluid transfer layer, and an absorbent inner core. The purpose of the fluid transfer layer, otherwise known as a surge layer, is to accommodate a surge of fluid and allow the absorbent core more time to absorb the surge. This prevents liquid overflow or other leaking from the product. An additional purpose of the surge layer is to isolate the top sheet from the absorbent core to minimize re-wetting of the top sheet from the absorbent core side (prevent "rewet").

Many proposals have been made for fluid surge layers. Generally, the use of bulky, high void volume fabrics that are resistant to wet compression has been proposed. The high bulk enhances the resistance to rewet, while the resistance to wet compression improving performance and allowing the layer to retain its properties after an initial wetting.

The non-woven surge layer fabrics proposed to date are disadvantageous in that they offer limited performance, and require relatively expensive and difficult manufacturing processes. There is therefore an unresolved need for an improved surge layer fabric as well as a method for making the same.

OBJECTS OF THE INVENTION

It is an object of the invention to provide a method for making a non-woven composite fabric useful as a fluid transfer layer.

It is a further object of the invention to provide a composite non-woven fabric useful as a fluid transfer layer.

It is a further object of the invention to provide a method for making an absorbent article having a composite non-woven fabric surge layer, as well as the article thereby made.

SUMMARY OF THE INVENTION

The present invention generally comprises a method for making a non-woven fluid transfer fabric, as well as the fabric produced thereby. The present invention further comprises an absorbent article having a composite non-woven fabric surge layer, as well as a method for making the article.

The method of the present invention generally comprises the steps of depositing a first spunbond web layer on a support, depositing a second spunbond web layer on the first web, with one of the web layers having a melting point higher than that of the other. The two layers are then thermally bonded to one another. During bonding, the difference in melting points causes a different amount of shrinkage to occur in the layers. This results in a "micro-bulking" of the bonded layers, as the lower melting point layer gathers a bit on the higher melting point layer due to a greater degree of shrinkage in the lower melting point layer. It is noted that as used herein the term "micro-bulked" is intended to refer to a condition whereby a slightly textured, bulked, crimped, or corrugated profile is present but is not apparent to the naked eye.

Thermal bonding of the two layers is followed by a mechanical bulking of the two layers to "macro-bulk" the composite fabric. It is noted that as used herein the term "macro-bulked" is intended to refer to a condition whereby a corrugated, crimped, or creped profile is apparent to the naked eye. Mechanical bulking can be achieved by a number of methods as are generally known in the art. A preferred method of bulking is a process known generally as the MICREX process. In this process, the composite web is passed between a roller and a blade, and combed into a creping chamber. Mechanical bulking occurs in the creping chamber as corrugation of the web occurs. The MICREX process is described in detail in U.S. Pat. No. 4,921,64; herein incorporated by reference.

Preferably, the first web layer is the lower melting point layer, with the second layer having a higher melting point. Preferably, the first web layer comprises spunbond poly (ethylene terephalate) ("PET") fibers having a denier 4–10, and has a basis weight of between about 10–30 gm/m$^2$. Most preferably, the first layer is comprised of PET fibers of about 6 denier, and has a basis weight between about 10–20 gm/m$^2$.

A preferred second layer is comprised of spunbond PET of 10–15 denier, and has a basis weight of between about 10–45 gm/m$^2$. Most preferably the second layer is comprised of fibers of about 12–15 denier, and has a basis weight between about 15–30 gm/m$^2$.

The resulting fabric of the invention is of high bulk, and has substantial resistance to compression deformation and pore structure collapse. The method of the invention is more economical than prior art methods that may require bi-component or carded webs.

The fabric of the invention generally comprises the fabric produced by the method of the invention. It comprises a composite non-woven web having a first spunbond layer, a second spunbond layer thermally bonded to the first layer, with the two layers having different melting points. The difference in melting points causes differential shrinkage of the layers through thermal bonding, with the fabric having a resultant micro-bulked profile. Preferably, the fabric also has a macro-bulked profile attained through mechanical corrugation.

Preferably, the first layer comprises spunbond PET fibers having a denier 4–10, and has a basis weight of between about 10–30 gm/m$^2$. Most preferably, the first layer is comprised of PET fibers of about 6, and has a basis weight between about 10–20 gm/m$^2$. The preferred second layer is comprised of spunbond PET of 10–15 denier, and has a basis weight of between about 10–45 gm/m$^2$. Most preferably the second layer is comprised of fibers of about 12–15 denier, and has a basis weight between about 15–30 gm/m$^2$.

An additional embodiment of the invention comprise an absorbent article having the composite fluid transfer fabric of the invention overlying an absorbent core. The absorbent article generally comprises a cover sheet, a surge layer comprising the composite fluid transfer fabric layer of the invention as described above, and an absorbent core. The preferred absorbent core comprises super absorbent polymer ("SAP").

The above brief description sets forth rather broadly the more important features of the present disclosure so that the detailed description that follows may be better understood, and so that the present contributions to the art may be better appreciated. There are, of course, additional features of the disclosure that will be described hereinafter which will form the subject matter of the claims appended hereto. In this respect, before explaining the several embodiments of the disclosure in detail, it is to be understood that the disclosure is not limited in its application to the details of the construction and the arrangements set forth in the following description or illustrated in the drawings. The present invention is capable of other embodiments and of being practiced and carried out in various ways, as will be appreciated by those skilled in the art. Also, it is to be understood that the phraseology and terminology employed herein are for description and not limitation.

DETAILED DESCRIPTION

Figure 1:
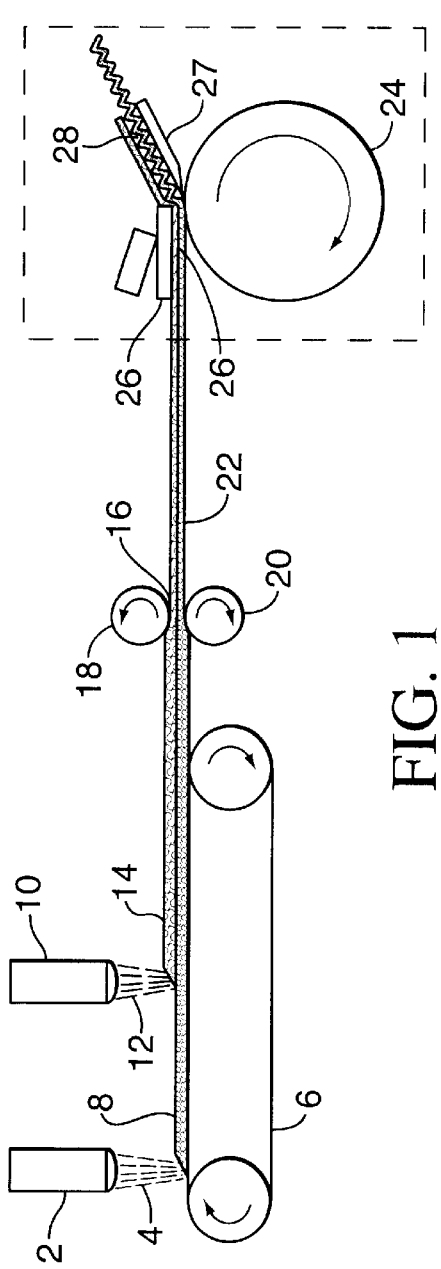
FIG. 1 is a schematic diagram showing a preferred embodiment of the method of the invention for producing a preferred fabric of the invention.

Turning now to the drawings, FIG. 1 is a schematic diagram useful for illustrating the steps of a preferred embodiment of the method of the invention and for describing the preferred fabric of the invention. A first beam 2 deposits spunbond PET filaments 4 on a moving support 6 to form a first non-woven spunbond layer 8. Preferred filaments 4 have a relatively large denier of 4–10, most preferably about 6. First non-woven layer 8 is preferably produced at a basis weight of 10–30 gm/m$^2$, most preferably between 10–20 gm/m$^2$.

Second beam 10 deposits spunbond PET filaments 12 to form second non-woven layer 14 overlaying first layer 8. Second non-woven layer 14 preferably has a basis weight of between 10–45 gm/m$^2$, most preferably 15–30 gm/m$^2$. Second layer 14 also preferably has a basis weight that is greater than that of first layer 8. Filaments 12 are preferably of 10–15 denier, and most preferably of 12–15 denier. PET is preferred for first and second layers 8 and 14 as it has been discovered that it has very good bulk retention characteristics.

While a preferred PET/PET bilayer web has been described as preferred, it will be appreciated that the invention may be practiced with any suitable combination of thermoplastics. As an example, although having less advantageous bulk retention characteristics, materials such as polypropylene may be used.

It is noted that first and second layers 8 and 14 are not illustrated to relative scale in FIG. 1; they are shown having an enhanced thickness for illustration purposes. It is also noted that FIG. 1 illustrates first layer 8 and second layer 14 being spunbond in line. This is a preferred embodiment of the method of the invention only; first and second layers may of course also be prepared off-line from one another.

It is critical to the method of the invention that first layer 8 have a different melting point than second layer 14. The difference in melting point of the layers 8 and 14 is at least 5° C.; and most preferably is at least 10° C. lower. First layer 8 preferably has a melting point lower than second layer 14.

After deposit on support 6, first and second layers 8 and 14 are then thermally bonded to one another. This is preferably achieved through thermal calender nip 16 between calender rolls 18 and 20. A thermally bond, composite web 22 results. Calender rollers 18 and 20 are operated at a temperature that depends on the materials being used, the basis weights used, the line speed, the fiber denier, as well as other factors as are known in the art. Generally, they preferably operate at a temperature sufficient to initiate melting in first layer 8.

Figure 2:
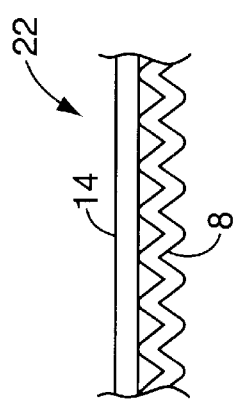
FIG. 2 illustrates the micro-bulked profile of the fabric of the invention resulting from thermal bonding of the two layers.

During the thermal bonding step, the lower melting point layer 8 fuses to a greater degree than higher melting point layer 14. This results in differential shrinkage occurring, with the result that the first layer 8, showing greater shrinkage, tends to gather on the second layer 14. FIG. 2 illustrates a profile of the resulting bonded composite, with first layer 8 showing gathering on second layer 14, which shows less shrinkage. This condition is referred to herein as "micro-bulked". Due to its greater basis weight and larger denier filaments, second layer 14 has a larger pore size than first layer 8.

It is preferred that wire side first layer 8 be the lower melting point layer to take advantage of the maximum loft and bulk of higher denier second layer 14 through the thermal bonding step. Further, it is preferred to have the lower melting point layer closer to the source of heat, which traditionally is on the wire side. It will be appreciated by those knowledgeable in the art that the arrangement of higher and lower melting point layers could be reversed.

Referring once again to FIG. 1, bonded composite web 22 is then subjected to a mechanical bulking step, which preferably comprises passing web 22 through a Micrex® process (Micrex® is a registered trademark of the of the Micrex Corporation, Walpole, Mass.). This preferred process of mechanical bulking, illustrated as occurring within the dashed lines of FIG. 1, is described in detail in U.S. Pat. Nos. 4,717,329; and 4,921,643, herein incorporated by reference. Generally, during the Micrexing process, web 22 is conveyed between rotating roll 24 and blade 26 converging toward the roll. Web 22 is conveyed into a conveying cavity 26 between blade 26 and roll 24, firmly gripped by comb blade 27, and conveyed along comb 27 into a main treatment cavity 28 where mechanical bulking takes place. As a result of this process, web 22 is imparted with a pronounced V-pleated, corrugation, or "macro-bulked" profile. Although the Micrex fluting is generally illustrated in FIG. 1 as occurring in a machine direction ("MD"), it may likewise be preferred to perform fluting in a cross direction ("CD") depending on an intended ultimate use of the web. It is further noted that micro-bulking may likewise take place in a CD or MD, depending on desired end uses.

While the Micrex process has been described as a preferred method for mechanically bulking web 22, it will be appreciated that many alternative methods exist and are known for mechanical bulking and are likewise suitable for practice of the invention. It is also noted that although FIG. 1 illustrates initial thermal bonding and mechanical bulking to occur at separate, successive stations, both micro and macro bulking could conceivably be achieved simultaneously.

Figure 3:
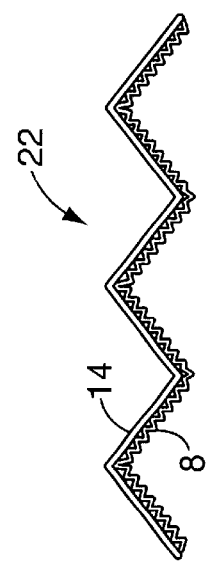
FIG. 3 illustrates the macro-bulked profile of the fabric of the invention resulting from mechanically bulking the bonded composite.

A profile of the resulting corrugated, micro-bulked and macro-bulked fabric web is illustrated in FIG. 3. The final web 22 has a pronounced corrugation from the Micrex process, with an additional micro-bulked surface profile resultant from the differential shrinkage through initial calendering.

Figure 4:
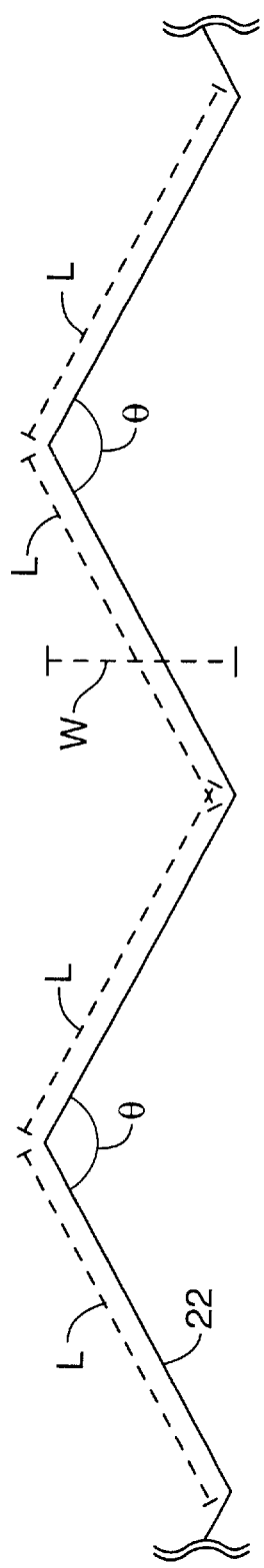
FIG. 4 illustrates the preferred fluting angle of the fabric of the invention.

It has been found that the most preferred degree of mechanical bulking for fabric stability is a corrugation pattern with one leg of corrugation approximately twice the fabric thickness. In other words, an angle of fluting of about 120° is most preferred. This is illustrated in FIG. 4, where the fabric thickness is represented as W, the length of a corrugation leg is represented as L, and the angle of fluting is represented as θ. As illustrated, with L=2×W, θ is equal to 120°.

Through the method of the invention, the combination of the differential shrinkage and mechanical bulking results in a high bulk fabric layer that simulates the crimping found in staple fiber webs, and allows for retention of loft after conversion. Further, the method allows for production of a fabric at lower costs than prior art surge layer fabrics. The preferred basis weights and deniers provide an open pore structure and compression resistance that are advantageous for a fluid transfer layer. In use as a fluid transfer layer, the fabric should be oriented with the second layer 14 facing the skin side to take advantage of its larger pore size.

The present invention further comprises an absorbent article utilizing the fluid transfer layer of the invention. The absorbent article of the invention may comprise, by way of example, a sanitary napkin, an adult incontinence product, or a diaper. The absorbent article of the invention comprises a porous cover sheet, the fluid transfer layer of the invention as described above underlying the cover sheet, and an absorbent core material. A most preferred core material comprises super absorbent polymer ("SAP"). It has been found that the surge layer of the invention is advantageous for use with SAP, as its resistance to pore structure collapse and high bulk resist SAP gel blocking, while providing efficient fluid distribution and wicking.

Figure 5:
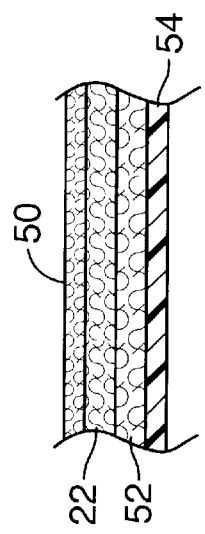
FIG. 5 is a cross section of a preferred absorbent article of the invention.

FIG. 5 illustrates a cross section of a preferred absorbent article of the invention. A topsheet 50 is uppermost for contact with a wearer's skin. Topsheet 50 is porous, compliant, soft feeling, and non-irritating to the skin. By way of example, topsheet 50 may comprise a non-woven spunbond polypropylene fabric. Surge or fluid transfer layer 22 comprises the fluid transfer layer of the invention as described herein, with its upper layer facing upwards toward topsheet 50, to take advantage of its larger pore size.

Absorbent core 52 underlies surge layer 22. Absorbent core 52 may comprise fibers capable of absorbing relatively large quantities of liquid, such as cellulose fibers or wood pulp. More preferably, core 52 comprises polymers capable of absorbing liquid many times their weight, as are known as super absorbent polymers. Super absorbent polymers may be employed in powdered or fiber form. Underlying core 52 is backsheet 54, which is preferably impervious to liquids, and may be manufactured for example from a plastic sheet. It is noted that the relative thickness's of the various layers are not illustrated to scale in FIG. 5.

A method for making a preferred absorbent article as illustrated in FIG. 5 comprises the steps of providing a topsheet 50, preparing underlying fluid transfer layer 22 of the invention as generally described herein above, and providing an absorbent core 52 underlying layer 22. Liquid impervious backsheet 54 is also preferably provided.

The advantages of the disclosed invention are thus attained in an economical, practical, and facile manner.

While preferred embodiments and example configurations have been shown and described, it is to be understood that various further modifications and additional configurations will be apparent to those skilled in the art. As an example, although the embodiments described herein use two web layers, other embodiments within the scope of the attached claims could be practiced with additional layers. It is intended that the specific embodiments and configurations herein disclosed are illustrative of the preferred and best modes for practicing the invention, and should not be interpreted as limitations on the scope of the invention as defined by the appended claims.

What is claimed is:

1. A method for making a non-woven composite web, comprising the steps of:
   a) depositing a first polyester spunbond layer on a support;
   b) depositing a second polyester layer on said first layer, said second layer having a melting point different than said first layer;
   c) thermally bonding said first layer and said second layer to one another to form a micro-bulked web consisting only of said first and second layers; and
   d) mechanically bulking said micro-bulked web.

2. A method for making a non-woven web as in claim 1, wherein said step of mechanically bulking said web comprises:
   a) conveying said micro bulked web between a rotating roll and a blade, said blade converging towards said roll;
   b) conveying said web along said roll into a conveying cavity; and
   c) removing and firmly gripping said web from said roll with a comb, said comb directing said web into a main treatment cavity where said web is corrugated.

3. A method for making a non-woven web as in claim 1, wherein said step of mechanically bulking said web imparts a corrugation in the cross direction.

4. A method for making a non-woven web as in claim 1, wherein said step of mechanically corrugating said web further comprising imparting an average angle of fluting of about 120°.

5. A method for making a non-woven web as in claim 1, wherein said first web comprises spunbond PET fibers of between 4–10 denier, and has a basis weight between 10–30 gm/m$^2$.

6. A method for making a non-woven web as in claim 5, wherein said first layer has a basis weight between about 10–20 gm/m$^2$.

7. A method for making a non-woven web as in claim 5, wherein said first web fiber denier is about 6.

8. A method for making a non-woven web as in claim 1, wherein said second layer comprises spunbond PET fibers of 10–15 denier, and has a basis weight of between about 10–45 gm/m$^2$.

9. A method for making a non-woven web as in claim 1, wherein said second layer comprises spunbond PET of between about 12–15 denier, and has a basis weight of between about 15–30 gm/m$^2$.

10. A method for making a non-woven web as in claim 1, wherein said first layer melting point is at least 5° C. different than said second layer melting point.

11. A method of making a non-woven web as in claim 1, wherein said first layer melting point is at least 10° C. different than said second layer melting point.

12. A method for making a non-woven web as in claim 1, wherein said first and second layers having different basis weights.

13. A method for making a non-woven composite web as in claim 1, wherein said step of thermally bonding said first and said second layers to one another comprises passing said first and second layers through a heated calender nip.

14. A method for making a non-woven fluid transfer layer as in claim 1, wherein said first and said second non-woven layers are produced in line.

15. A method for making a non-woven fluid transfer layer, comprising the steps of:
   a) spunbonding PET fibers of 4–10 denier to form a first non-woven web layer with a basis weight of between about 10–20 gm/m$^2$;
   b) spunbonding PET fibers of 10–15 denier to form a second non-woven web layer, said second web having a basis weight greater than said first web and less than about 30 gm/m$^2$, having a melting point at least about 10° C. greater than the melting point of said first web layer;
   c) thermally bonding said first and second web layers to one another in a calender nip; and
   d) mechanically corrugating said thermally bonded layers.

16. A method for making a non-woven fluid transfer layer as in claim 15, wherein said first spunbond layer is deposited on a support, and said second layer is deposited on said first layer prior to thermal bonding.

17. A method for making an absorbent article, comprising the steps of:

a) making a fluid transfer layer through steps comprising:
   i) depositing a first non-woven web layer on a support, said first layer comprising a spunbond web of PET fibers of 4–10 denier, with a basis weight of between about 10–20 gm/m$^2$;
   ii) depositing a second non-woven web layer on said first web, said second web comprising a spunbond web of PET fibers of 10–15 denier, having a basis weight greater than said first web, having a melting point at least about 10° C. greater than the melting point of said first web layer;
   iii) thermally bonding said first and second web layers to one another in a heated calender nip, said thermal bonding imparting a micro-bulked profile due to differential shrinkage;
   iv) mechanically bulking said thermally bonded layers to impart a macro-bulked profile;
b) overlaying said fluid transfer layer with a porous cover sheet; and
c) underlying said fluid transfer layer with an absorbent core.

18. A method for making an absorbent article as in claim 17, wherein said absorbent core is comprised of a super absorbent polymer.

* * * * *